(12) United States Patent
Kobayashi

(10) Patent No.: US 7,214,827 B2
(45) Date of Patent: May 8, 2007

(54) METHOD FOR FRIEDEL-CRAFTS ACYLATION OF ANILIDES

(75) Inventor: Shu Kobayashi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 11/194,554

(22) Filed: Aug. 2, 2005

(65) Prior Publication Data

US 2005/0267315 A1    Dec. 1, 2005

Related U.S. Application Data

(63) Continuation of application No. 10/250,861, filed as application No. PCT/JP02/00020 on Jan. 8, 2002, now abandoned.

(30) Foreign Application Priority Data

Jan. 9, 2001    (JP) .............................. 2001-001914

(51) Int. Cl.
*C07C 215/00* (2006.01)
(52) U.S. Cl. ...................................... 564/443
(58) Field of Classification Search ................. 564/443
See application file for complete search history.

(56) References Cited

FOREIGN PATENT DOCUMENTS

| | | |
|---|---|---|
| JP | 5-320089 | 12/1993 |
| JP | 6-135883 | 5/1994 |
| JP | 2001-145833 | 5/2001 |

OTHER PUBLICATIONS

I. Hachiya, "Hafnium (IV) trifluoromethanesulfonate, an efficient catalyst for the Friedel-Crafts acylation and alkylation reactions", Bull. Chem. Soc. Jpn., 68(7), 2053-60, 1995.
J. Matsuo, et al., "Gallium nonafluorobutanesulfonate as an efficient catalyst in Friedel-Crafts acylation", Synlett, 2000(3), 403-405, 2000.
S. Kobayashi et al., "Catalytic Friedel-Crafts acylation of benzene, chlorobenzene, and fluorobenzene using a novel catalyst system, hafnium triflate and trifluoromethanesulfonic acid", Tetrahedron Lett., 39 (26), 4697-4700, 1998.
Kobayashi et al., Tetrahedron, vol. 56, pp. 6463-6465, 2000.
Front page of Advanced Synthesis & Catalysis, vol. 343, No. 1, Jan. 2001.
Shū Kobayashi et al., "Catalytic Friedel-Crafts Acylation of Aniline Derivatives", Adv. Synth. Catal., 343, No. 1, pp. 71-74, 2001.

*Primary Examiner*—Shailendra Kumar
(74) *Attorney, Agent, or Firm*—Wenderoth, Lind & Ponack, L.L.P.

(57) ABSTRACT

An anilide is reacted with an acylating agent by using as a catalyst a tri(perfluoroalkane sulfonate) compound of any of the elements belonging to groups 3 to 5 and groups 13 to 15 in periods 4 to 6 of the periodic table, thereby bonding an acyl group to the benzene ring. Thus, ketoaniline derivatives, which are useful as physiologically active compounds or intermediates in synthesizing the same, are synthesized in high reaction yield by catalytic acylation.

16 Claims, No Drawings

US 7,214,827 B2

METHOD FOR FRIEDEL-CRAFTS ACYLATION OF ANILIDES

This application is a continuation application of Ser. No. 10/250,861 filed Aug. 13, 2003, now abandoned, which is a 371 application of PCT/JP02/00020 filed Jan. 8, 2002.

TECHNICAL FIELD

The present invention relates to a method for the Friedel-Crafts acylation of anilides. More specifically, the present invention relates to a novel method of Friedel-Crafts acylation that enables the synthesis of ketoanilides useful as physiologically active compounds or intermediates for the synthesis of the same, in high reaction yield through catalytic reaction.

BACKGROUND ART

Friedel-Crafts acylation has been known to be a basic and useful method of preparing aromatic ketones. For Friedel-Crafts acylation, a catalytic amount of Lewis acid is used, while in acylation, more than a stoichiometric amount of Lewis acid such as $AlCl_3$ is normally required. However, environmental problems that needs to be considered are evoked by the large amount of aluminum residue derived from $AlCl_3$, especially in industrial-scale processes. For solving such problems, several types of excellent catalysts have been developed, and catalytic acylation of active benzenes such as anisole, xylene and toluene have been realized. However, the realization of catalytic Friedel-Crafts acylation of benzene and inactive benzenes such as chlorobenzene has still been difficult. Under these circumstances, in recent years, Dubac et al. and the present inventor's group have found and reported in the following literature that $Bi(OTf)_3$, $Hf(OTf)_4$ and the like are effective catalysts for the Friedel-Crafts acylation of benzene and inactive benzenes.

TABLE 1

(a) Desmurs, J. R.; Labrouillere, M.; Roux, C. L.; Gaspard, H.; Laporterie, A.; Dubac, J. Tetrahedron Lett. 1997, 38, 8871.
(b) Repichet, S.: Roux, C. L.; Dubac, J.; Desmurs, J. -R. Eur. J. Org. Chem. 1998, 2743.

TABLE 2

(a) Hachiya, I.; Moriwaki, M.; Kobayashi, S. Tetrahedron Lett. 1995, 36, 409. (b) Hachiya, I.; Moriwaki, M.; Kobayashi, S. Bull. Chem. Soc. Jpn. 1995, 68, 2053. (c) Kobayashi, S.; Iwamoto, S. Tetrahedron Lett. 1998, 39, 4697.

Further, quite recently, the present inventors have found that gallium catalysts, especially gallium tri(perfluoroalkane sulfonate), exhibits the highest activity in Friedel-Crafts acylation (Matsuo, J.; Odashima, K.; Kobayashi, S. Synlett 2000, 403).

Meanwhile, it has been found that ketoaniline structures are important in physiologically active compounds and fine chemicals, and the realization of means to efficiently synthesize these compounds while controlling their structures, has become an important subject. However, while the Friedel-Crafts acylation of aniline derivatives is a simple and clear method of introducing an acyl group into a benzene ring, and while a novel Friedel-Crafts acylation method for the synthesis of aromatic ketones has been realized by the present inventor's group as stated above, actual examples of a catalytic reaction have not yet been reported.

Accordingly, the present invention aims to provide, under the foregoing circumstances, a novel Friedel-Crafts acylation method that enables the synthesis of ketoaniline derivatives useful as physiologically active compounds or intermediates thereof, in high reaction yield through catalytic reaction.

DISCLOSURE OF THE INVENTION

In order to solve the foregoing problems, the present invention firstly provides a method for Friedel-Crafts acylation of anilide, which comprises reacting an anilide with an acylating agent, using as a catalyst a tri(perfluoroalkane sulfonate) compound of an element that belongs to any one of periods 4 to 6 of the periodic table, that also belongs to any one of groups 3 to 5 or groups 13 to 15, thereby bonding an acyl group to a benzene ring.

Further, the present invention provides secondly, the method for Friedel-Crafts acylation of anilide, wherein the catalyst is one or more tri(perfluoroalkane sulfonate) compound(s) of an element selected from the group consisting of Ga, Sc, In, Y, Lanthanoids, Zr, Hf, Sn, Pb, Nb, Ta, Sb and Bi; thirdly, the method for Friedel-Crafts acylation of anilide, wherein the reaction is performed in a nitroalkane solvent containing a perchlorate or a halogenated hydrocarbon solvent; fourthly, the method for Friedel-Crafts acylation of anilide, wherein the perchlorate is an alkali metal perchlorate; and fifthly, the method for Friedel-Crafts acylation of anilide, wherein the acylating agent is an acid anhydride, an acid halide, an ester or a carboxylic acid.

Still further, the present invention sixthly provides the method for Friedel-Crafts acylation of anilide, wherein an anilide represented by the following formula (1)

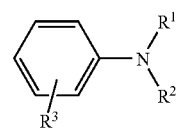

(1)

(wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the aforementioned acyl group; $R^3$ represents a substituent bonded to the benzene ring, and $R^3$ may be absent) with an acylating agent represented by the following formula (2)

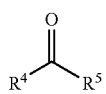

(2)

(wherein $R^4$ represents a hydrocarbon group that may contain a substituent; and $R^5$ represents —O—CO—Rb, in which Rb is a hydrocarbon group that may contain a substituent, a halogen atom or —OH) thereby synthesizing an acylanilide represented by the following formula (3)

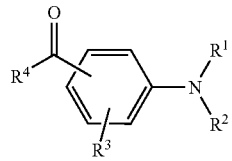

(3)

(wherein $R^1$, $R^2$, $R^3$ and $R^4$ are as defined above).

The difficulty encountered in the Friedel-Crafts acylation of aniline derivatives is considered to be attributed to the decrease in activation of the Lewis acid catalyst, or rather, the deactivation of the Lewis acid catalyst, caused by the basic nitrogen of the amino group in the aniline derivatives. In fact, even in conventional reaction methods that use a large amount of $AlCl_3$, acylation barely occurs.

On the contrary, the above-described present invention dramatically improves the reaction yield and facilitates the introduction of an acyl group to anilides as aniline derivatives.

BEST MODE FOR CARRYING OUT THE INVENTION

The present invention has the foregoing characteristics, and hereinafter, embodiments are described.

In the present invention, an anilide, that is, a compound containing at least one acyl group bonded to the amino group of aniline, is reacted with an acylating agent to bond the acyl group to the benzene ring.

In this acylation reaction, a tri(perfluoroalkane sulfonate) compound of an element that belongs to any one of periods 4 to 6 of the periodic table while also belonging to groups 3 to 5 or groups 13 to 15 of the periodic table is used as a catalyst. This compound is used as a Lewis acid catalyst that is active specifically in the Friedel-Crafts acylation of the anilide. Of course, the catalyst compounds can be used singularly or in combination. As the element constituting such catalyst compounds, for example, Ga, Sc, In, Y, lanthanoid, Zr, Hf, Sn, Pb, Nb, Ta, Sb and Bi may be exemplified. Further, as the perfluoroalkane sulfonate, perfluoroalkane sulfonates containing about 1 to 10 carbon atoms, such as trifluoromethane sulfonate (—OTf) and nonafluorobutane sulfonate (—ONf) may be exemplified.

Of these catalyst compounds, Ga tri(perfluoroalkane sulfonates), Sc tri(perfluoroalkane sulfonates), Hf tri(perfluoroalkane sulfonates). Sb tri(perfluoroalkane sulfonates) and Bi tri(perfluoroalkane sulfonates) are exemplified, and Ga tri(perfluoroalkane sulfonates) such as Ga(OTf), and $Ga(ONf)_3$ may be listed as catalyst compounds that are especially active. Such catalyst compounds may be used in a catalytic amount; normally, an amount such as 1 to 50 mol % of the reaction substrate or preferably, 5 to 20 mol % of the reaction substrate may be considered.

In the present invention, together with the catalyst compound, the presence of a solvent may be considered. Although the reaction may be conducted without the use of a solvent, a nitroalkane solvent that contains a perchlorate or a halogenated hydrocarbon solvent is preferably used as the solvent for the acylation of this invention.

As the nitroalkane solvent, various compounds such as nitromethane and nitroethane may be considered. These may be used either singularly or in combination. However, with nitroalkane alone, the desired reaction activity can not be obtained. As described above, when a nitroalkane solvent is used, it is used after adding perchlorate. This addition dramatically increases the reaction yield.

As the perchlorate, alkali metal perchlorates such as $LiClO_4$, $KClO_4$ and $NaClO_4$ are preferable. Of these, $LiClO_4$ is especially effective.

When these perchlorates are in the form of alkali metal salts, they are commonly used as 1 to 10 M nitroalkane solutions.

As the halogenated hydrocarbon solvent, for example, 1,2-dichloroethane and the like may be used. Regarding these halogenated hydrocarbon solvents, an excellent effect is exhibited to provide high acylation yield, especially when acid halide is used as the acylating agent.

Regarding the anilide as the reaction substrate, the acyl group bonded to the amino group of aniline not only includes carbonyl group (—CO—), but may also include various groups such as sulfonyl group (—$SO_2$—) and carbonyl group (—OCO—).

Further, as the acylating agent used in the reaction, various compounds such as acid anhydrides, acid halides, esters and carboxylic acids may be used. As mentioned above, when an acid halide is used, a halogenated hydrocarbon solvent may effectively be used. Moreover, when a carboxylic acid is used, the addition of a trifluoroacetic anhydride is effective.

Various acylanilides are synthesized in high yield by the method of the present invention. Specifically, for example, the acylanilide represented by the above formula (3) is synthesized by the reaction of the anilide of the above formula (1) with the acylating agent of the above formula (2).

When $R^1$, $R^2$ and Ra in the anilide of formula (1) are hydrocarbon groups that may contain a substituent, the hydrocarbon group may be an aliphatic, alicyclic or aromatic hydrocarbon group, and may contain various substituents as long as they do not inhibit the acylation reaction. This is the same for $R^4$ and Rb in formula (2) that represents the acylating agent.

Further, $R^3$ representing the substituent attached to the benzene ring in the anilide of formula (1) may be absent, or it may be a substituent such as a hydrocarbon group or an alkoxy group, that does not inhibit the acylation reaction. A plurality of the same type or different types of such groups may be bonded to the benzene ring.

In the method of the present invention, the acyl group may selectively be bonded to the para- or meta-position of the anilide by the presence of substituent $R^3$ and by selecting $R^1$ and $R^2$.

Regarding the ratio of the anilide as the reaction substrate and the acylating agent, the anilide/acylating agent ratio, in terms of molar ratio, may usually be in the range of 1/10 to 10/1, preferably 2/10 to 10/5. For a nitroalkane solvent, the reaction temperature may be in the range of 5 to 60° C., and for a halogenated hydrocarbon solvent, the reaction temperature may be as high as its reflux temperature. The reaction may be conducted in atmospheric pressure or under increased pressure. The atmosphere may be inert gas-atmosphere such as $N_2$ or Ar.

Hereinafter, the present invention is described in more detail by referring to the following Examples. Of course, the description is not limited by the following Examples.

EXAMPLES

Example 1

The Friedel-Crafts acylation of acetoanilide was conducted using a Ga Lewis acid catalyst according to the following reaction scheme.

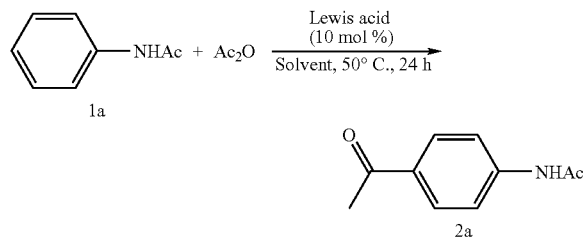

The results are shown in Table 3.

As a typical example of the reaction procedure, that of entry No. 4 in Table 3 is described:

That is, to a solution obtained by stirring acetylanilide (108 mg, 0.80 mmol), $LiClO_4$ (1.28 mg, 12.0 mmol), acetic anhydride (168 mg, 1.65 mmol) and nitromethane (2.0 mL) was added 10 mol % of $Ga(OTf)_4$ (41.5 mg, 0.08 mmol) based on the amount of acetylanilide as the reaction substrate. The mixture was stirred at 50° C. for 24 hours, after which the reaction mixture was cooled with saturated aqueous $NaHCO_3$ (10 mL). The aqueous layer was extracted with $CH_3Cl_2$ (3×15 mL). The combined organic layer was dried over $Na_2SO_4$, and the concentrated residue was subjected to column chromatography on silica gel (50/1—$CHCl_3$/MeOH) to obtain a colorless solid product 2a (131 mg, 93%).

TABLE 3

| Entry | Lewis acid | Solvent (Media) | Yield (%) |
|---|---|---|---|
| 1 | $Ga(OTf)_3$ | $CH_3NO_2$ | 3 |
| 2 | $Ga(OTf)_3$ | $MeNO_2$—$LiClO_4$ (3 M) | 62 |
| 3 | $Ga(OTf)_3$ | $MeNO_2$—$LiClO_4$ (4.8 M) | 82 |
| 4 | $Ga(OTf)_3$ | $MeNO_2$—$LiClO_4$ (6 M) | 93 |
| 5 | $Ga(ONf)_3$ | $MeNO_2$—$LiClO_4$ (6 M) | 90 |
| 6 | $GaCl_3$ | $MeNO_2$—$LiClO_4$ (6 M) | 33 |

From Table 3, it was found that in the reaction of acetoanilide (1a) with acetic anhydride using 10 mol % of $Ga(OTf)_3$, $Ga(OTf)_3$ in itself shows extremely low reaction activity in nitromethane ($MeNO_2$) as shown in Entry No. 1, whereas the addition of lithium perchlorate ($LiClO_4$) dramatically increases the reaction yield. As the amount of $LiClO_4$ increased, the yield of fraction product 2a increased; the acetylation product 2a was obtained in a yield of 93% in a 6.0 M $MeNO_2$—$LiClO_4$ solution, as shown in Entry No. 4.

As shown in Entry No. 5, it was verified that gallium tri(nonafluorobutane sulfonate) ($Ga(ONf)_3$) also acts as an effective catalyst. However, the catalytic activity of $GaCl_3$ was low.

Incidentally, the identification results of the above-described acylation product 2a were as follows:

TABLE 4

2a: Mp 169–171° C. $^1H$ NMR($CDCl_3$) δ
2.22(s, 3H), 2.58(s, 3H), 7.63(d, J=8.8Hz, 2H), 7.75(brs, 1H),
7.94(d, J=8.8Hz, 2H): $^{13}C$ NMR($CDCl_3$) δ
24.81 26.48, 118.85, 129.76, 132.80, 142.35, 168.68, 197.11.

Example 2

The acylation reaction was conducted in the manner described in Example 1 using other catalysts such as $Sc(OTf)_3$, $Sc(ONf)_3$, $Hf(OTf)_3$, $Sb(OTf)_3$ and $Bi(OTf)_3$. The results are shown in Table 5. The same acetylation product 2a was obtained.

Here, $AlCl_3$, a typical Lewis acid for Friedel-Crafts acylation used as a Comparative Example was not effective. In a $MeNO_2$—$LiClO_4$ solution, even $AlCl_3$ of more than a stoichiometric amount barely showed reaction activity. In addition, when the reaction was performed using acetic anhydride in 1,2-dichloroethane in the presence of 3.2 equivalents of $AlCl_3$ at 50° C. for 12 hours, an acetylation product was obtained at a yield of 9%.

TABLE 5

| Lewis acid | Solvent (Media) | Yield (%) |
|---|---|---|
| $Sc(OTf)_3$ | $MeNO_2$—$LiClO_4$ (6 M) | 10 |
| $Sc(ONf)_3$ | $MeNO_2$—$LiClO_4$ (6 M) | 48 |
| $Hf(OTf)_4$ | $MeNO_2$—$LiClO_4$ (6 M) | 44 |
| $Sb(OTf)_3$ | $MeNO_2$—$LiClO_4$ (6 M) | 59 |
| $Bi(OTf)_3$ | $MeNO_2$—$LiClO_4$ (6 M) | 59 |
| $AlCl_3$[a] | $MeNO_2$—$LiClO_4$ (6 M) | <1 |
| none | $MeNO_2$—$LiClO_4$ (6 M) | <1 |
| $AlCl_3$[b] | $ClCH_2CH_2Cl$ | 9 |

[a]$AlCl_3$ (5.1 equiv) was used.
[b]$AlCl_3$ (3.2 equiv) was used. The reaction time was 12 h.

Example 3

The acylation reaction was conducted as described in Example 1 using various anilides and acylating agents. $Ga(OTf)_3$ and $Ga(ONf)_3$ were used as the catalyst. The results are shown in Table 6.

TABLE 6

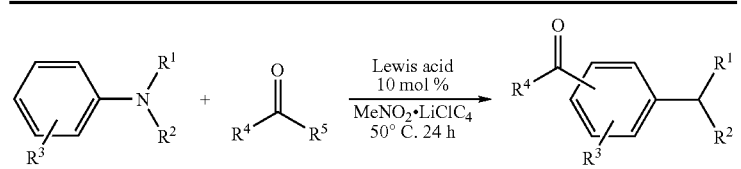

| Entry | Lewis acid | $R^1$ | $R^2$ | $R^3$ | | $R^4$ | $R^5$ | Product | Yield (%) |
|---|---|---|---|---|---|---|---|---|---|
| 1 | $Ga(OTf)_3$ | Ac | H | H | (1a) | Me | OAc | 2a | 93 |
| 2 | $Ga(OTf)_3$ | Bz | H | H | (1b) | Me | OAc | 2b | quant |
| 3 | $Ga(OTf)_3$ | Bz | H | H | (1b) | Et | OCOEt | 2c | 95 |
| 4 | $Ga(OTf)_3$ | Bz | H | H | (1b) | i-Pr | OCOi-Pr | 2d | 74 (83)[a] |
| 5 | $Ga(OTf)_3$ | Ms | Me | H | (1c) | Me | OAc | 2e | 97 |

TABLE 6-continued

| Entry | Lewis acid | $R^1$ | $R^2$ | $R^3$ | | $R^4$ | $R^5$ | Product | Yield (%) |
|---|---|---|---|---|---|---|---|---|---|
| 6 | Ga(OTf)$_3$ | Ac | H | o-Me | (1d) | Me | OAc | 2f | 61[a] |
| 7 | Ga(OTf)$_3$ | Ac | H | o-OMe | (1e) | Me | OAc | 2g | 75[a,b] |
| 8 | Ga(ONf)$_3$ | Ms | Me | o-OMe | (1f) | Me | OAc | 2h | 79 |
| 9 | Ga(OTf)$_3$ | Ac | H | m-Me | (1g) | Me | OAc | 2i | 62 |
| 10 | Ga(ONf)$_3$ | Ms | Me | m-Me | (1h) | Me | OAc | 2j | 62 |
| 11 | Ga(ONf)$_3$ | Ms | Me | m-OMe | (1i) | Me | OAc | 2k | 78 |
| 12 | Ga(OTf)$_3$ | MS | Me | p-OMe | (1j) | Me | OAc | 2l | 54[a] |
| 13 | Ga(OTf)$_3$ | Ms | Me | H | (1c) | Ph | Cl | 2m | quant[c,d] |
| 14 | Ga(ONf)$_3$ | i-BuOCO | H | H | (1k) | Ph | Cl | 2n | 80[c] |
| 15 | Ga(OTf)$_3$ | Bz | H | H | (1b) | Me | OH | 2b | 90[a] |

[a]Twenty mol % at the catalyst was used.
[b]Regioisomer 2g' was obtained in 5% yield.
[c]The reaction was carried out in 1,2-dichloromethane under reflux for 24 h.
[d]After the acylation, the crude product was treated with 25% HBr/AcOH.
[e]Trifluoroacetic anhydride was added.

In this Table 6, reaction products 2a, 2b, 2c, 2d, 2e, 2f, 2i, 2j and 2k were all products in which the acyl group R$^4$—CO— is bonded to the p-(para) position of the benzene ring. Meanwhile, reaction product 2g was obtained as a mixture with 2g' as shown below.

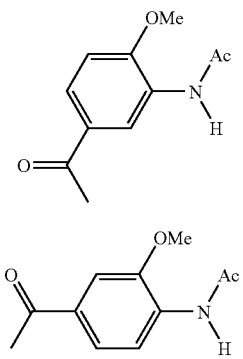

Further, reaction products 2h and 2l indicate the following products.

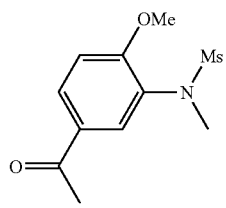

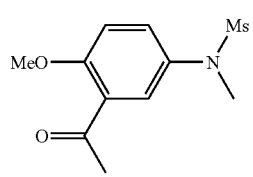

In all entries, the reaction proceeded smoothly in the presence of a catalytic amount of the gallium compound in MeNO$_2$—LiClO$_4$ and showed excellent yield. Acetoanilide (1a), a well as benzanilide (1b) reacted with certain acetic anhydrides to obtain the corresponding acylation product in high yield.

Further, N-methanesulfonyl (MS)-N-methylaniline (1c) was reacted with acetic anhydride in the presence of 10 mol % of Ga(OTf)$_3$ to obtain acylation product 2e in a 97% yield. Some o- and m-substituted aniline derivatives also provided acylation products in high yield in the presence of a catalytic amount of Ga(OTf)$_3$ or G(ONf)$_3$.

In the benzoylation reaction, 1c and 1k reacted smoothly with benzoyl chloride in 1,2-dichloroethane under reflux for 24 hours to give the desired products (2m and 2n) in high yield. When carboxylic acid was used as the acylating agent, the desired acylation product (2b) was obtained in excellent yield without the formation of a trifluoroacetylation adduct, by adding trifluoroacetic anhydride.

Identification results for compounds 2b to 2n as the reaction products were as shown in Tables 7, 8 and 9.

TABLE 7

2b: $^1$H NMR(CDCl$_3$) δ 2.60(s, 3H), 2.58(s, 3H), 7.26–8.02(m, 10H); $^{13}$C NMR(CDCl$_3$) δ 26.48, 119.24, 127.07, 128.97, 129.85, 132.31, 133.17, 134.48, 142.26, 165.75, 196.90.
Zc: Mp 189–191° C.(lit$^2$ 187–188° C.). $^1$H NMR(CDCl$_3$) δ 1.23(t, J=7.3Hz, 3H), 2.99(q, J=7.3Hz, 2H), 7.49(t, J=7.3Hz, 2H), 7.58(t, J=7.3Hz. 1H), 7.76(d, J=8.7Hz, 1H), 7.88(d, J=7.3Hz, 1H), 7.99(d, J=8.7Hz, 1H), 8.06–8.14(bs, 1H); $^{13}$C NMR(CDCl$_3$) δ 8.3, 31.6, 119.3, 127.1, 128.9, 129.4, 132.2, 132.9, 134.5, 142.1, 165.8, 199.7.
2d: $^1$H NMR(CDCl$_3$) δ 1.16(d, J=6.6Hz, 6H), δ 3.50(m, 1H), 7.25–7.50(m, 3H), 7.80–7.93(6s,

TABLE 7-continued

6H), 9.30–9.48(m, 1H): $^{13}$C NMR(CDCl$_3$) δ 18.99, 19.22, 34.88, 119.70, 127.18, 128.35, 129.34, 131.39, 131.79, 134.21, 142.56, 166.60, 203.70.
2e: $^1$H NMR(CDCl$_3$) δ 2.61(s, 3H), 2.87(s, 3H), 3.38(s, 3H), 7.49(d, J=8.8Hz, 2H), 7.99(d, J=8.8Hz, 2H); $^{13}$C NMR(CDCl$_3$) δ 26.64, 35.79, 37.56, 124.67, 129.49, 135.13, 145.53, 196.92, MS(EI) m/z 227(M$^+$)
2f: Mp 142–144° C.(lit.$^3$ 141–142° C.), $^1$H NMR(CDCl$_3$) δ 2.24(s, 3H), 2.32(s, 3H), 2.57(s, 3H), 7, 12–7.22(bs, 1H), 7.78–7.83(m, 2H), 8.10–8.19(m, 1H); $^{13}$C NMR(CDCl$_3$) δ 17.6, 17.7, 24.4, 36.36, 26.38, 121.6, 127.5, 130.4, 133.1, 140.4, 168.6, 197.4.

TABLE 8

2g: Mp 119–120° C.(lit.$^4$ 122.5° C.), $^1$H NMR(CDCl$_3$) δ 2.23(s, 3H), 2.58(s, 3H), 3.95(s, 3H). 6.93(d, J=8.6Hz. 1H), 7.74(dd, J=8.6, 22Hz. 1H), 8.99(d, J=2.2Hz, 1H); $^{13}$C NMR(CDCl$_3$) δ 24.9, 26.5, 56.0, 109.5, 120.4, 124.4, 127.4, 130.5, 151.2, 168.3, 197.2.
2h: Mp 125–127° C. $^1$H NMR(CDCl$_3$) δ 2.57(s, 3H), 2.97(s, 3H), 3.27(s, 3H), 3.98(s, 3H). 7.00(d. J=8.4Hz. 1H), 7.97(d, J=2.2Hz. 1H), 7.99(dd, J=8.4, 2,2Hz. 1H); $^{13}$C NMR(CDCl$_3$) δ 26.4, 37.6, 38.2, 56.0, 111.7, 129.1, 130.4, 130.9, 132.9, 159.9, 196.0
2i: Mp 131–133° C.(lit.$^5$ 135–136° C.), $^1$H NMR(CDCl$_3$) δ 2.20(s, 3H), 2.51(s, 3H), 2.56(s, 3H), 7.32(s, 1H), 7.57(d, J=8.4Hz. 1H), 7.71(d, J=8.4Hz. 1H), 8.08–8.18(bs, 1H); $^{13}$C NMR(CDCl$_3$) δ 22.1, 24.6, 29.2, 116.3, 122.3, 131.4, 132.7, 140.6, 141.0, 168.9, 200.3.
2j: Mp 111–114° C. $^1$H NMR(CDCl$_3$) δ 2.55(s, 314), 2.58(s, 3H), δ 2.87(s, 3H). 3.35(s, 3H). 7.24(d, J=2.3Hz. 1H), 7.31(dd, J=8.4, 2.3Hz, 1H), 7.73(d, J=8.4Hz. 1H); $^{13}$C NMR(CDCl$_3$) δ 21.8, 29.5, 35.8, 37.6, 122.2, 128.0, 130.5, 135.8, 140.2, 143.9, 200.4.
2k: Mp 83–85° C. $^1$H NMR(CDCl$_3$) δ 2.62(s, 3H), 2.86(s, 3H), 3.35(s, 3H), 3.94(s, 3H), 6.92(dd, J=8.5, 2.0Hz. 1H), 7.13(d, J=2.0Hz. 1H), 7.78(d, J=8.5Hz, 1H); $^{13}$C NMR(CDCl$_3$) δ 31.8, 35.5, 37.6, 55.8, 110.1, 115.1, 126.5, 131.3, 146.2, 159.4, 198.5.

TABLE 9

2l: Mp 112–114° C. $^1$H NMR(CDCl$_3$) δ 2.63(s, 3H), 2.84(s, 3H), 3.30(s, 3H), 3.94(s, 3H). 7.00(d, J=5.5Hz, 1H), 7.56(dd, J=5.5, 1.8Hz. 1H), 7.70(d, J=1.8Hz. 1H); $^{13}$C NMR(CDCl$_3$) δ 31.8, 35.1, 38.2, 55.9, 112.6, 126.8, 128.2, 133.8, 134.2, 158.2, 198.5.
2m: $^1$H NMR(CDCl$_3$) δ 2.99(d, J=5.1Hz. 3H), 4.88–4.95(bs, 1H), 7.41–7.58(m, 3H), 7.66 7.77(m, J=8.6, 4H), 8.02(d, J=2.0Hz, 1H); $^{13}$C NMR(CDCl$_3$) δ 30.3, 108.8, 109.0. 126.7, 128.2, 129.4, 131.5, 132.1, 135.0, 138.6, 149.3, 194.0.
2n: $^1$H NMR(CDCl$_3$) δ 0.98(d, J=6.8Hz. 6H), 2.00(d, J=6.8Hz. 1H), 3.99(d, J=6.8Hz. 2H), 6.84–6.87(bs. 1H), 7.44–7.61(m, 5H), 7.74–7.85(m, 4H); $^{13}$C NMR(CDCl$_3$) δ 19.0. 27.9, 71.7, 113.6, 117.5, 128.2, 129.8, 131.7, 132.1, 137.9, 142.2, 153.3, 195.6.

INDUSTRIAL APPLICABILITY

As has been described in detail above, according to the present invention, a Friedel-Crafts acylation method that enables the synthesis of ketoaniline derivatives useful as physiologically active compounds or intermediates for the synthesis of the same, in high reaction yield by catalytic acylation is provided.

The invention claimed is:

1. A method for Friedel-Crafts acylation of anilide, which comprises reacting an anilide with an acylating agent in the presence of a perchlorate, using as a catalyst a tri(perfluoroalkane sulfonate) compound of an element selected from the group consisting of Ga, Sb and Bi, thereby bonding an acyl group to a benzene ring.

2. The method for Friedel-Crafts acylation of anilide of claim 1, wherein the reaction is performed in a nitroalkane solvent or a halogenated hydrocarbon solvent.

3. The method for Friedel-Crafts acylation of anilide of claim 1, wherein the perchiorate is an alkali metal perchlorate.

4. The method for Friedel-Crafts acylation of anilide of claim 2, wherein the perchlorate is an alkali metal perchlorate.

5. The method for Friedel-Crafts acylation of anilide of claim 1, wherein the acylating agent is an acid anhydride, an acid halide, an ester or a carboxylic acid.

6. The method for Friedel-Crafts acylation of anilide of claim 2, wherein the acylating agent is an acid anhydride, an acid halide, an ester or a carboxylic acid.

7. The method for Friedel-Crafts acylation of anilide of claim 3, wherein the acylating agent is an acid anhydride, an acid halide, an ester or a carboxylic acid.

8. The method for Friedel-Crafts acylation of anilide of claim 4, wherein the acylating agent is an acid anhydride, an acid halide, an ester or a carboxylic acid.

9. The method for Friedel-Crafts acylation of anilide of claim 1, wherein an anilide represented by the following formula (1)

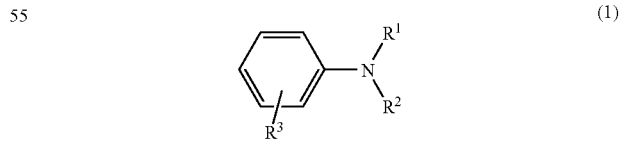

(1)

wherein R$^1$ and R$^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of R$^1$ and R$^2$ being the acyl group; and R$^3$ represents a substituent bonded to the benzene ring, and $R^3$ may be absent, is reacted with an acylating agent represented by the following formula (2)

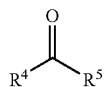

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

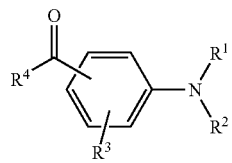

(3)

wherein $R^1$, $R^2$, $R^3$ and $R^4$ are as defined above.

10. The method for Friedel-Crafts acylation of anilide of claim 2, wherein an anilide represented by the following formula (1)

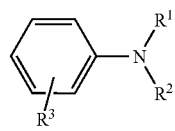

(1)

wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

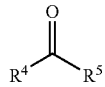

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

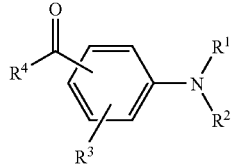

(3)

wherein $R^1$, $R^2$, $R^3$ and $R^4$ are as defined above.

11. The method for Friedel-Crafts acylation of anilide of claim 3, wherein an anilide represented by the following formula (1)

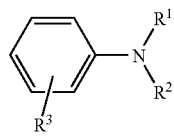

(1)

wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

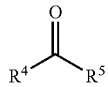

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

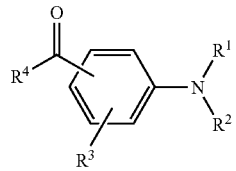

(3)

wherein $R^1$, $R^2$, $R^3$ and $R^4$ are as defined above.

12. The method for Friedel-Crafts acylation of anilide of claim 4, wherein an anilide represented by the following formula (1)

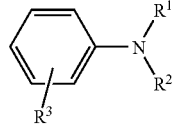

(1)

wherein $R^1$ and $R^2$ each represent a hydrogen atom, a hydrocarbon group that may contain a substituent, or an acyl group represented by Ra—CO—, Ra—SO$^2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

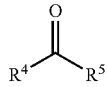

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

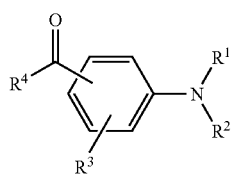

(3)

wherein $R^1$, $R^2$, $R^3$ and $R^4$ are as defined above.

13. The method for Friedel-Crafts acylation of anilide of claim 5, wherein an anilide represented by the following formula (1)

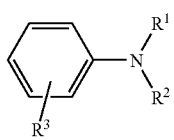

(1)

wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

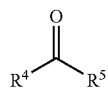

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

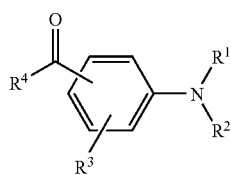

(3)

wherein $R^1$, $R^2$, $R^3$ and $R^4$ are as defined above.

14. The method for Friedel-Crafts acylation of anilide of claim 6, wherein an anilide represented by the following formula (1)

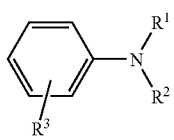

(1)

wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

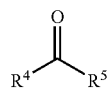

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

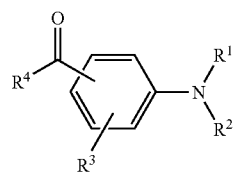

(3)

wherein $R^1$, $R^2$, $R^3$ and $R^4$ are as defined above.

15. The method for Friedel-Crafts acylation of anilide of claim 7, wherein an anilide represented by the following formula (1)

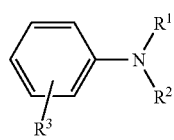

(1)

wherein $R^1$ and $R^2$ each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of $R^1$ and $R^2$ being the acyl group; and $R^3$ represents a substituent bonded to the benzene ring, and $R^3$ may be absent, is reacted with an acylating agent represented by the following formula (2)

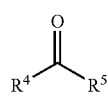

(2)

wherein $R^4$ represents a hydrocarbon group that may contain a substituent; and $R^5$ represents —O—CO—Rb, in which Rb is a hydrocarbon group that may contain a substituent, a halogen atom or —OH, thereby synthesizing an acylanilide represented by the following formula (3)

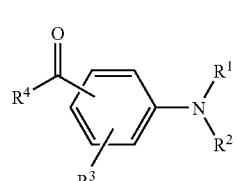

(3)

wherein $R^1$, $R^2$, $R^3$ and $R^4$ are as defined above.

16. The method for Friedel-Crafts acylation of anilide of claim 8, wherein an anilide represented by the following formula (1)

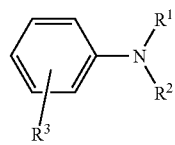
(1)

wherein R¹ and R² each represent a hydrogen atom, a hydrocarbon group that may contain a substituent, or an acyl group represented by Ra—CO—, Ra—SO$_2$— or Ra—OCO—, in which Ra represents a hydrocarbon group that may contain a substituent, at least one of R¹ and R² being the acyl group; and R³ represents a substituent bonded to the benzene ring, and R³ may be absent, is reacted with an acylating agent represented by the following formula (2)

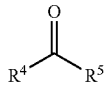
(2)

wherein R⁴ represents a hydrocarbon group that may contain a substituent; and R⁵ represents —O—CO—Rb, in which Rb is a hydrocarbon group that may contain a substituent, a halogen atom or —OH, thereby synthesizing an acylanilide represented by the following formula (3)

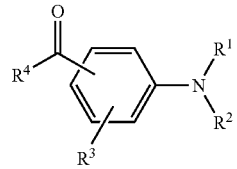
(3)

wherein R¹, R², R³ and R⁴ are as defined above.

* * * * *